US010073021B2

(12) United States Patent
Rykaczewski (10) Patent No.: US 10,073,021 B2
(45) Date of Patent: Sep. 11, 2018

(54) SYSTEMS AND METHODS FOR GENERATION AND OBSERVATION OF PENDANT DROPLETS BY PREFERENTIAL CONDENSATION

(71) Applicant: Konrad Rykaczewski, Tempe, AZ (US)

(72) Inventor: Konrad Rykaczewski, Tempe, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 172 days.

(21) Appl. No.: 15/232,507

(22) Filed: Aug. 9, 2016

(65) Prior Publication Data

US 2016/0349164 A1    Dec. 1, 2016

Related U.S. Application Data

(63) Continuation of application No. PCT/US2015/017052, filed on Feb. 23, 2015.

(60) Provisional application No. 61/944,346, filed on Feb. 25, 2014.

(51) Int. Cl.
*G01N 13/02*    (2006.01)

(52) U.S. Cl.
CPC ..... *G01N 13/02* (2013.01); *G01N 2013/0208* (2013.01); *G01N 2013/0241* (2013.01)

(58) Field of Classification Search
CPC ........... G01N 13/02; G01N 2013/0208; G01N 2013/0241; G01N 2013/0258
See application file for complete search history.

(56) References Cited

U.S. PATENT DOCUMENTS

| | | | |
|---|---|---|---|
| 5,861,946 A * | 1/1999 | Hudson | G01N 13/02 356/138 |
| 6,446,878 B1 | 9/2002 | Chandra et al. | |
| 6,674,076 B1 | 1/2004 | Orfino et al. | |
| 6,857,309 B2 * | 2/2005 | Mansky | B01J 19/0046 506/12 |
| 2002/0079089 A1 | 6/2002 | Kang et al. | |
| 2006/0196968 A1 | 9/2006 | Rabin et al. | |

FOREIGN PATENT DOCUMENTS

| | | |
|---|---|---|
| JP | 2008-256330 | 10/2008 |
| KR | 1020080091715 | 10/2008 |

OTHER PUBLICATIONS

International Search Report and Written Opinion for PCT/US15/17052, dated May 27, 2015.

(Continued)

*Primary Examiner* — Justin Olamit
(74) *Attorney, Agent, or Firm* — Snell & Wilmer L.L.P.

(57) ABSTRACT

Systems and methods for droplet generation are suitable for use in connection with goniometers. Via preferential condensation, droplets of a variety of liquids may be formed at a variety of temperatures and pressures, eliminating the need for expensive and complex conventional droplet generation systems. Condensation and evaporation of a droplet may be controlled in order to evaluate advancing and receding contact angles in the goniometer.

12 Claims, 5 Drawing Sheets

(56) References Cited

OTHER PUBLICATIONS

K. Rykaczewski et al., "Methodology for Imaging Nano-to-Microscale Water Condensation Dynamics on Complex Nanostructures", ACS Nano, vol. 5, No. 7, pp. 5962-5968, 2011.
C. Dietz et al., "Visualization of Droplet Departure on a Superhydrophobic Surface and Implications to Heat Transfer Enhancement during Dropwise Condensation", Applied Physical Letters, 97, 033104, 2010.
K. Rykaczewski et al., "Direct Imaging of Complex Nano- to Microscale Interfaces Involving Solid, Liquid, and Gas Phases", ACS Nano, vol. 6, No. 10, pp. 9326-9334, 2012.
K. Rykaczewski et al., "Electron Beam Heating Effects during Environmental Scanning Electron Microscopy Imaging of Water Condensation on Superhydrophobic Surfaces", Applied Physical Letters, 98, 093106, 2011.
N. Miljkovic et al., "Effect of Droplet Morphology on Growth Dynamics and Heat Transfer during Condensation on Superhydrophobic Nanostructured Surfaces", ACS Nano, vol. 6, No. 2, pp. 1776-1785, 2012.
R. Ranganathan, "Surface Activity and Effects as Measured by Contact Angle", Thesis—Master of Science in Electrical Engineering, Texas Tech University, 2003.
C. Philipp et al., "Liquid Droplet Growth in Humid Air Environment Including Techniques for the Embryo Detection", 8th World Conference on Experimental Heat, Transfer, Fluid Mechanics, and Thermodynamics, Lisbon, Portugal, Jun. 16-20, 2013.
International Search Report and Written Opinion for International Application No. PCT/US2015/017052 dated May 27, 2015.

* cited by examiner

SYSTEMS AND METHODS FOR GENERATION AND OBSERVATION OF PENDANT DROPLETS BY PREFERENTIAL CONDENSATION

CROSS-REFERENCE TO RELATED APPLICATIONS

This application is a continuation of PCT Application No. PCT/US2015/017052 filed on Feb. 23, 2015 and entitled "SYSTEMS AND METHODS FOR GENERATION AND OBSERVATION OF PENDANT DROPLETS BY PREFERENTIAL CONDENSATION". PCT Application No. PCT/US2015/017052 claims priority to, and the benefit of, U.S. Provisional Application Ser. No. 61/944,346 filed on Feb. 25, 2014 and entitled "CONDENSATION BASED CONTACT ANGLE GONIOMETER". Both of the above applications are hereby incorporated by reference in their entirety.

TECHNICAL FIELD

The present disclosure relates to surface science, and in particular to droplet generation in connection with goniometers utilized therein.

BACKGROUND

Manipulation of liquids in small quantities, particularly at conditions departing significantly from ambient, remains a challenging problem. In particular, generation of liquid droplets, for example for use with a contact angle goniometer, in conditions departing significantly from ambient, typically requires complex, expensive equipment. Accordingly, improved droplet generation systems remain desirable.

SUMMARY

In an exemplary embodiment, a droplet generation system comprises a temperature control component, a thermal insulator, and a thermal conductor coupled to the temperature control component. The thermal conductor is disposed at least partially within the thermal insulator and has a tip portion not surrounded by the thermal insulator. The tip portion is configured to form, via condensation, a droplet thereon responsive to operation of the temperature control component and responsive to exposure of the tip portion to a vapor.

In another exemplary embodiment, a contact angle goniometer system comprises an enclosed chamber, a sample stage configured to receive sample material thereon, and a droplet generation system. The droplet generation system comprises a first temperature control component, a thermal insulator, and a thermal conductor coupled to the temperature control component. The thermal conductor is disposed at least partially within the thermal insulator and has a tip portion not surrounded by the thermal insulator.

In another exemplary embodiment, a method of using a contact angle goniometer system comprises filling an enclosed chamber of the contact angle goniometer system with vapor, adjusting a temperature of a thermal conductor so as to form a droplet of condensate on a tip portion of the thermal conductor, positioning the tip portion and a sample stage relative to one another such that the droplet simultaneously contacts the tip portion and the sample material, and observing a contact angle between the droplet and a sample material.

The contents of this summary section are provided only as a simplified introduction to the disclosure, and are not intended to be used to limit the scope of the appended claims.

BRIEF DESCRIPTION OF THE DRAWINGS

With reference to the following description and accompanying drawings.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments, including the best mode. As will become apparent, various changes may be made in the function and arrangement of the elements described in these embodiments without departing from the scope of the present disclosure.

For the sake of brevity, conventional techniques for liquid droplet generation, surface characterization, goniometer design and/or use, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical system for droplet generation by preferential condensation and/or a contact angle goniometer incorporating the same.

In a typical goniometer operating at ambient conditions, static and dynamic contact angles are measured by observing surface interaction with a small drop dispensed through a pipette. This approach is problematic at conditions significantly departing from ambient in which small quantities of liquid are not easily manipulated. While several other methods for measuring surface and interfacial energies at elevated pressures exist, ability to measure the static and dynamic contact angles is particularly desirable for condensation studies.

In contrast to the shortcomings of prior approaches, principles of the present disclosure contemplate systems and methods whereby droplet generation may be effectively and efficiently accomplished by preferential condensation. Rather than utilizing complex, expensive high pressure liquid dispensing systems, in various exemplary embodiments, such droplets may be utilized, for example, in a contact angle goniometer system.

Figure 1:
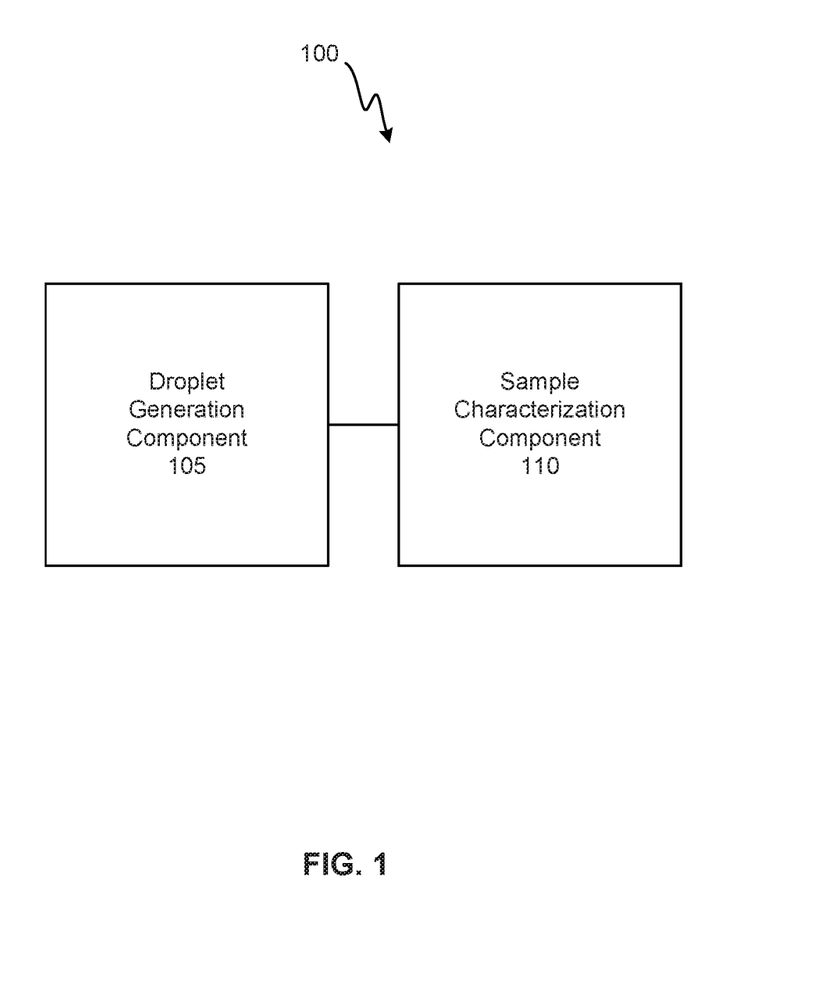
FIG. 1 illustrates a block diagram of an exemplary contact angle goniometer in accordance with various embodiments.

With reference now to FIG. 1, a goniometer system 100 may be any system configured to assess contact angles arising between a droplet and a sample. In an exemplary embodiment, a goniometer system 100 comprises a droplet generation component 105 and a sample characterization component 110. Goniometer system 100 may also comprise various structural and/or supporting components, for example vapor chambers and the like, as is known in the art.

Figure 2:
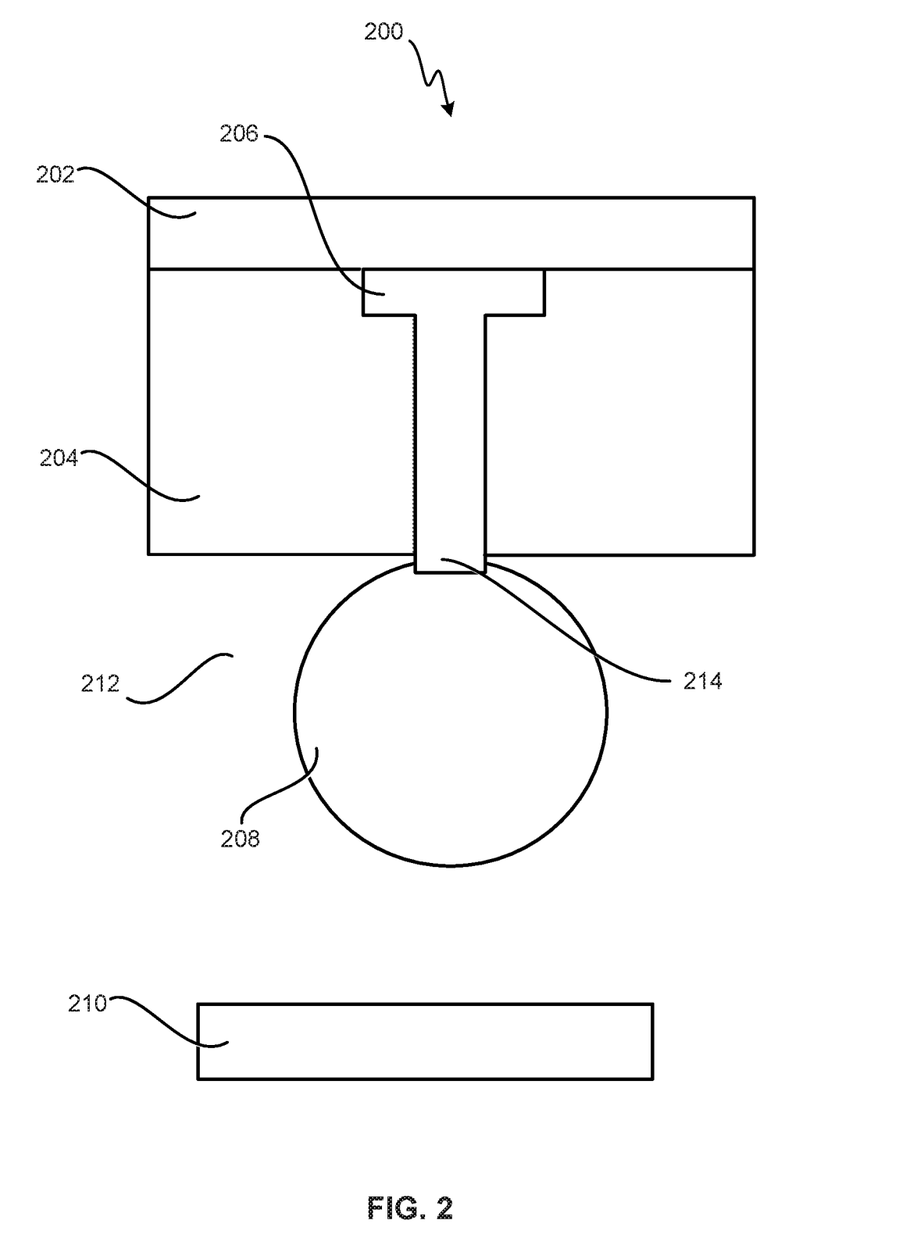
FIG. 2 illustrates a schematic view of an exemplary droplet generation system in accordance with various embodiments.

With reference now to FIG. 2, in various exemplary embodiments a droplet generation system 200 comprises a temperature control component 202, a thermal insulator 204, and a thermal conductor 206. Thermal insulator 204 may preferably be hydrophobic, and thermal conductor 206 may preferably be hydrophilic. Droplet generation system 200 may be utilized to form one or more droplets 208 via condensation of a vapor 212. Droplets 208 may be applied to a sample 210, as desired, for example in order to characterize the interaction between droplet 208 and sample 210.

Temperature control component 202 is configured to heat or cool thermal conductor 206. In various exemplary embodiments, temperature control component 202 comprises a thermoelectric component such as a peltier heat pump. Temperature control component 202 may be configured to heat or cool thermal conductor 206 to a desired temperature, or allow thermal conductor 206 to obtain a range of temperatures, as desired. Temperature control component 202 may be configured to increase or decrease the temperature of thermal conductor 206 over a desired range and/or within a desired precision and accuracy, for example within a fraction of a degree.

In other exemplary embodiments, temperature control component 202 comprises a liquid or gas flow heat exchanger. In these exemplary embodiments, temperature control component 202 may be configured to heat or cool thermal conductor 206 indirectly by placing it in thermal contact, but not physical contact, with a gas or liquid having a temperature different than that of thermal conductor 206. In various exemplary embodiments, temperature control component 202 may utilize a flow of a cooling or cryogenic fluid, for example, liquid nitrogen or nitrogen gas. Moreover, temperature control component 202 may comprise any suitable component configured to heat or cool thermal conductor 206.

Thermal insulator 204 is configured to at least partially encapsulate, insulate, and/or isolate other components of droplet generation system 200, for example temperature control component 202 and/or a tip portion 214 thereof. In an exemplary embodiment, thermal insulator 204 comprises polytetrafluoroethylene having a thickness of between about 0.5 cm and about 2.5 cm. However, thermal insulator 204 may be of any thickness suitable to insulate desired components of droplet generation system 200. In other exemplary embodiments, thermal insulator 204 comprises a polymeric and/or ceramic material having thermally insulating properties. Thermal insulator 204 may be comprised of any material suitable for insulating desired components of droplet generation system 200. Thermal insulator 204 is preferably hydrophobic in order to resist formation and/or spreading of droplets thereon.

Thermal conductor 206 is configured to provide a location for preferential condensation. In an exemplary embodiment, thermal conductor 206 comprises copper. In other exemplary embodiments, thermal conductor 206 comprises a metal or alloy having high thermal conductivity, for example aluminum and/or the like. Moreover, thermal conductor 206 may comprise any material having suitable thermal conductivity to encourage preferential condensation thereon.

In various exemplary embodiments, thermal conductor 206 is configured with a tip portion 214. Tip portion 214 may be integrally formed with thermal conductor 206; moreover, tip portion 214 may also be removable and/or replaceable, as desired, in order to provide greater flexibility in droplet generation in connection with a variety of vapors, temperatures, and pressures. In various exemplary embodiments, thermal conductor 206 is partially surrounded by thermal insulator 204. Tip portion 214 is at least partially exposed through (i.e., not completely surrounded by) thermal insulator 204. In some embodiments, tip portion 214 of thermal conductor 206 may be approximately flush with a surface of thermal insulator 204. In other exemplary embodiments, tip portion 214 may extend beyond a surface of thermal insulator 204, for example as illustrated in FIG. 2.

Figure 3A:
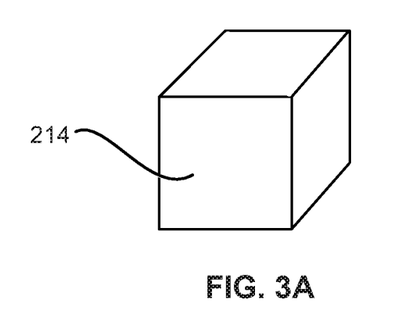
FIGS. 3A, 3B, and 3C illustrate perspective views of exemplary tip portions of a droplet generation system in accordance with various embodiments.
Figure 3B:
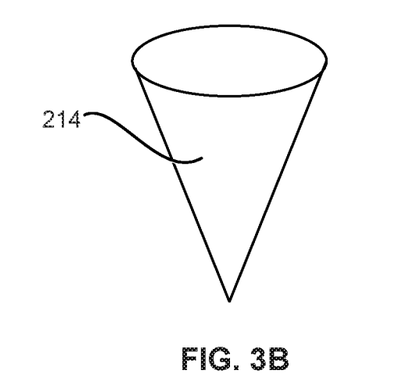
Figure 3C:
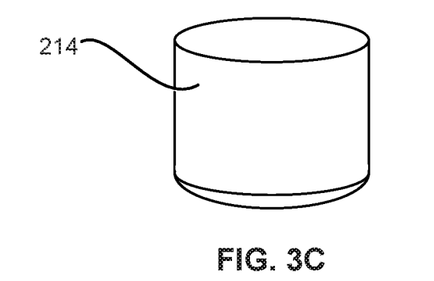

In various exemplary embodiments, tip portion 214 may have a diameter between about 1 mm and about 5 mm. With momentary reference to FIGS. 3A, 3B, and 3C, in certain exemplary embodiments, tip portion 214 may be square, conical, or elliptical in shape. In other exemplary embodiments, tip portion 214 may be cuboid, pyramidal, tapered, needle-like, and/or otherwise shaped and/or configured to generate a droplet of a desired volume and/or mass. Moreover, tip portion 214 may have any diameter and be any shape suitable for preferential condensation of droplets 208 thereon. Thermal conductor 206 and tip portion 214 are preferably hydrophilic in order to encourage formation of droplets 208 thereon.

In various exemplary embodiments, during operation of droplet generation system 200, temperature control component 202 is operated to generate a reduced temperature (for example, a temperature of about 10 degrees Celsius or below) on a face of temperature control component 202 abutting thermal conductor 206. The tip portion 214 of thermal conductor 206, which is not completely surrounded by (and/or extends beyond a surface of) thermal insulator 204, is exposed to a vapor 212. Droplets are desirably formed from vapor 212. In certain exemplary embodiments, vapor 212 may comprise air saturated with water vapor and having a temperature of between about 30 degrees Celsius and about 80 degrees Celsius. In other exemplary embodiments, vapor 212 may comprise (i) methane at a temperature less than 162 Kelvin and a pressure greater than 101 kiloPascals (kPa), (ii) ethane at a temperature less than 300 Kelvin and a pressure greater than 1 megaPascal (MPa), (iii) butane at a temperature less than 320 Kelvin and a pressure greater than 0.5 MPa, (iv) propane at a temperature less than 300 Kelvin and a pressure greater than 1 MPa, (v) carbon dioxide at a temperature less than 250 Kelvin and a pressure greater than 2.5 MPa, or the like. Moreover, any suitable vapor 212, temperature range, and/or pressure range may be utilized in order to form a droplet or droplets 208 on the tip portion 214 of thermal conductor 206.

Principles of the present disclosure and exemplary systems and methods disclosed herein are suitable for testing wetting properties of a variety of compounds, for example carbon dioxide and hydrocarbon liquids, including at pressures departing significantly from 1 atmosphere of pressure and/or at cryogenic temperatures. Table 1 lists some of the fluids whose wetting properties may be characterized in accordance with principles of the present disclosure. To test their wetting properties, the temperature of the tip portion 214 of thermal conductor 206 is decreased below the saturation temperature at a given pressure. In Table 1, the triple point of each fluid and surface tension at those conditions are presented to provide the lowest operational boundary for sample temperature and the highest reference point for liquid surface tension. In turn, the critical pressure and temperature are included to provide the highest bound for these parameters.

TABLE 1

List of exemplary fluids with relevant properties.
T and P are (subscript t and c corresponding to triple and critical point, respectively) temperature and pressure and σ is the surface tension in vicinity of the triple point.

|  | Carbon Dioxide ($CO_2$) | Methane ($CH_4$) | Ethane ($C_2H_6$) | Propane ($C_3H_8$) | Butane ($C_4H_{10}$) | Pentane ($C_5H_{12}$) |
| --- | --- | --- | --- | --- | --- | --- |
| $T_t$ (K) | 217 | 90 | 90 | 85 | 134 | 143 |
| $P_t$ (kPa) | 517 | 11.7 | 0.0008 | 1e−7 | 0.0007 | 7.6e−5 |
| $T_c$ (K) | 304 | 191 | 305 | 396 | 425 | 470 |
| $P_c$ (MPa) | 7.4 | 4.7 | 4.9 | 4.3 | 3.8 | 3.4 |
| $\sigma_t$ (mN/m) | 16.4 | 17 | 32 | 37 | 32 | 26 |

In various exemplary embodiments, droplet generation system 200 may be utilized to form droplets, for example water droplets, having a diameter of between about 10 micrometers and about 5 millimeters. In general, to test wetting properties, it is desirable to keep the diameter of a droplet below the capillary length, which is equal to square root of the ratio of surface tension and the product of density and gravitational constant. This ensures that effects of gravity are negligible. Typically, the capillary length is on the order of a few millimeters (for example, capillary length of water at 20° C. and 1 atmosphere is about 3 mm). In certain exemplary embodiments, droplet generation system 200 is usable to generate droplets 208 of about 1 mm in diameter. Millimeter-scale droplets 208 may be formed on the tip portion 214 of thermal conductor 206. For characterization of surface tension, droplets 208 may be larger, allowing gravity to deform them. The surface tension of the liquid may then be obtained from the geometry of the deformed drop at a given size.

Figure 4:
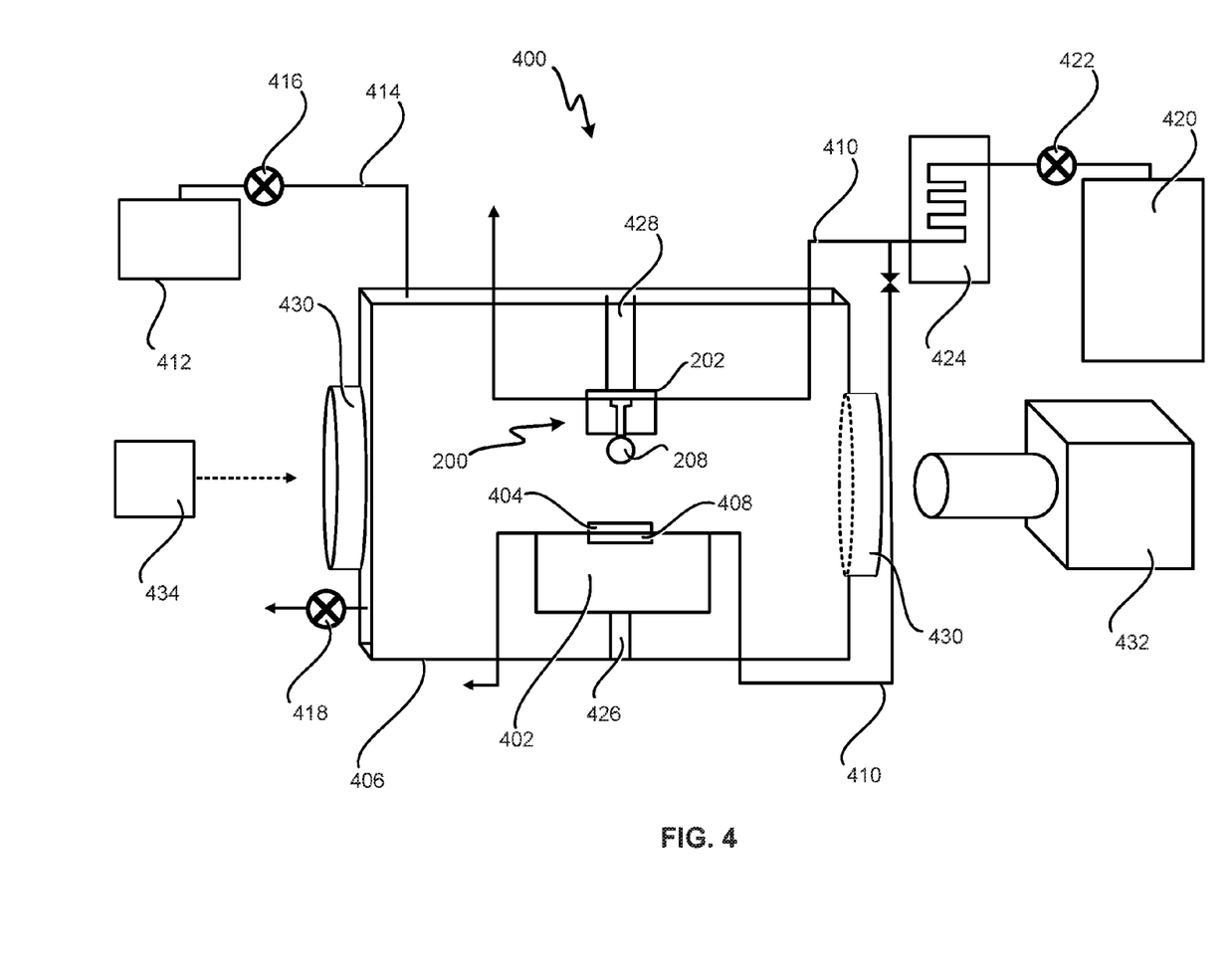
FIG. 4 illustrates a schematic view of an exemplary contact angle goniometer system in accordance with various embodiments.

Turning now to FIG. 4, in various exemplary embodiments, droplet generation system 200 may be utilized as part of a contact angle goniometer system 400. Goniometer system 400 may comprise a sample stage 402 disposed below droplet generation system 200. Goniometer system 400 may be configured to observe and/or record interactions of droplets 208 with a sample material 404. In certain exemplary embodiments, sample stage 402 may comprise a hydrophobic material. In other exemplary embodiments, sample stage 402 may comprise a thermally conductive material. Sample material 404 may comprise any suitable material whose interaction with a droplet 208 is desired to be characterized.

Goniometer system 400 may further comprise an enclosed chamber 406 at least partially surrounding sample stage 402 and droplet generation system 200. Enclosed chamber 406 may be configured to withstand high internal pressures and/or low temperatures, for example temperatures below 77 Kelvin and/or pressures up to about 30 atmospheres (approx. 3.04 MPa). Advantageously, depending on materials and construction, goniometer system 400 may be operable over any suitable range of temperatures and pressures, for example ranges including and/or bounded by the triple and critical points of a fluid or fluids (see Table 1).

In certain exemplary embodiments, enclosed chamber 406 may be in fluid communication with a vapor chamber 412. Vapor chamber 412 may be configured to surround or create liquid vapor from a desired medium. In certain exemplary embodiments, fluid communication between vapor chamber 412 and enclosed chamber 406 may occur through a vapor circuit 414. Stated differently, vapor circuit 414 may be configured to carry vapor from vapor chamber 412 to enclosed chamber 406. Vapor chamber 412 and/or vapor circuit 414 may be configured to withstand temperatures and pressures significantly departing from ambient conditions.

In various exemplary embodiments, goniometer system 400 may further comprise a vapor valve 416 and/or a release valve 418. The rate of vapor flow from vapor chamber 412 into enclosed chamber 406 may be varied by vapor valve 416. The rate of vapor flow from inside enclosed chamber 406 to a location external of enclosed chamber 406 may be varied by release valve 418.

With reference now to FIGS. 2 and 4, goniometer system 400 may further comprise at least one temperature control component 202 and/or 408. Fine adjustments of the temperature of tip portion 214 and/or sample material 404 may allow control of droplet 208 volume and/or mass through condensation and/or evaporation. Observation and/or measurement of advancing contact angles is possible during increase in volume and/or mass of droplet 208. Observation and/or measurement of receding contact angles is possible during decrease in volume and/or mass of droplet 208.

In certain exemplary embodiments, temperature control component 202 may be configured to adjust the temperature of tip portion 214 by balancing resistive heating and cooling, for example using a thermoelectric element. In other exemplary embodiments, temperature control component 408 may be configured to adjust the temperature of sample stage 402 and/or sample material 404 by balancing resistive heating and cooling, for example using a thermoelectric element. In certain exemplary embodiments, one or more of temperature control component 202 and/or 408 may comprise a peltier heat pump.

In certain exemplary embodiments, temperature control components 202 and/or 408 may comprise a liquid or gas flow heat exchanger. Such a heat exchanger may be configured to adjust the temperature of tip portion 214, the temperature of sample stage 402, and/or the temperature of sample material 404, by circulating a primary thermal medium 420 through a flow circuit 410. Primary thermal medium 420 may comprise a liquid, gas, or other suitable medium configured to transfer heat indirectly. In certain exemplary embodiments, flow circuit 410 may be configured to carry primary thermal medium 420 from outside enclosed chamber 406 to inside enclosed chamber 406. In certain exemplary embodiments, flow circuit 410 may be configured to carry liquid or gas in a continuous circuit. Flow circuit 410 may be configured to bring liquid or gas having a different temperature into thermal contact with tip portion 214, sample stage 402, and/or sample material 404. In certain exemplary embodiments, goniometer system 400 may further comprise a thermal medium valve 422. The rate of flow of primary thermal medium 420 through flow circuit 410 may be varied by thermal medium valve 422.

Primary thermal medium 420 may be heated or cooled to a desired temperature before being brought into thermal contact with tip portion 214, sample stage 402, and/or sample material 404. In an exemplary embodiment, flow circuit 410 and primary thermal medium 420 therein may be brought into thermal contact with a secondary thermal medium 424. In certain embodiments, secondary thermal medium 424 may comprise liquid nitrogen or other suitable medium having a low temperature. In other exemplary embodiments, secondary thermal medium 424 may comprise a medium having a suitably high temperature.

With continued reference to FIGS. 2 and 4, in various exemplary embodiments goniometer system 400 further comprises at least one positioning mechanism 426 and/or 428. In various exemplary embodiments, a first positioning mechanism 426 may be coupled to sample stage 402. First positioning mechanism 426 may be configured to adjust the height and/or tilt of sample stage 402. Advantageously, adjusting the height of sample stage 402 may allow droplet 208 to approach sample material 404 at a controlled rate. Adjusting the tilt of sample stage 402 may allow observation and/or measurement of a sliding angle of droplet 208.

In certain exemplary embodiments, a second positioning mechanism 428 may be coupled to droplet generation system 200. Second positioning mechanism 428 may be configured to adjust the location of droplet generation system 200 (and particularly, the location of tip portion 214) with respect to a sample 404. Advantageously, adjusting the location of tip portion 214 may allow droplet 208 to approach sample material 404 at a controlled rate.

In various exemplary embodiments, goniometer system 400 comprises a mechanism for observation and measurement of droplet 208 during interaction with sample material 404. In certain exemplary embodiments, enclosed chamber 406 may comprise at least one window 430. Window 430 may comprise a transparent or translucent material configured to withstand high internal pressures and/or low temperatures. Window 430 may be disposed in a lateral face of enclosed chamber 406. In certain exemplary embodiments, goniometer system 400 further comprises a camera 432. Camera 432 may be configured to observe and/or capture images of droplet 208 during interaction with sample material 404. Moreover, camera 432 may be configured to observe geometry of a pendant droplet 208 to facilitate determination of surface tension. In certain exemplary embodiments, goniometer system 400 further comprises a light-generating component 434. Light-generating component 434 may be configured to illuminate a target area, for example, droplet 208 during interaction with sample material 404. In an exemplary embodiment, enclosed chamber 406 comprises first and second windows 430 disposed in opposing lateral faces of enclosed chamber 406, camera 432 disposed adjacent to the first window and oriented so as to capture images of droplet 208, and light-generating component 434 disposed adjacent to the second window and oriented so as to illuminate droplet 208.

Figure 5:
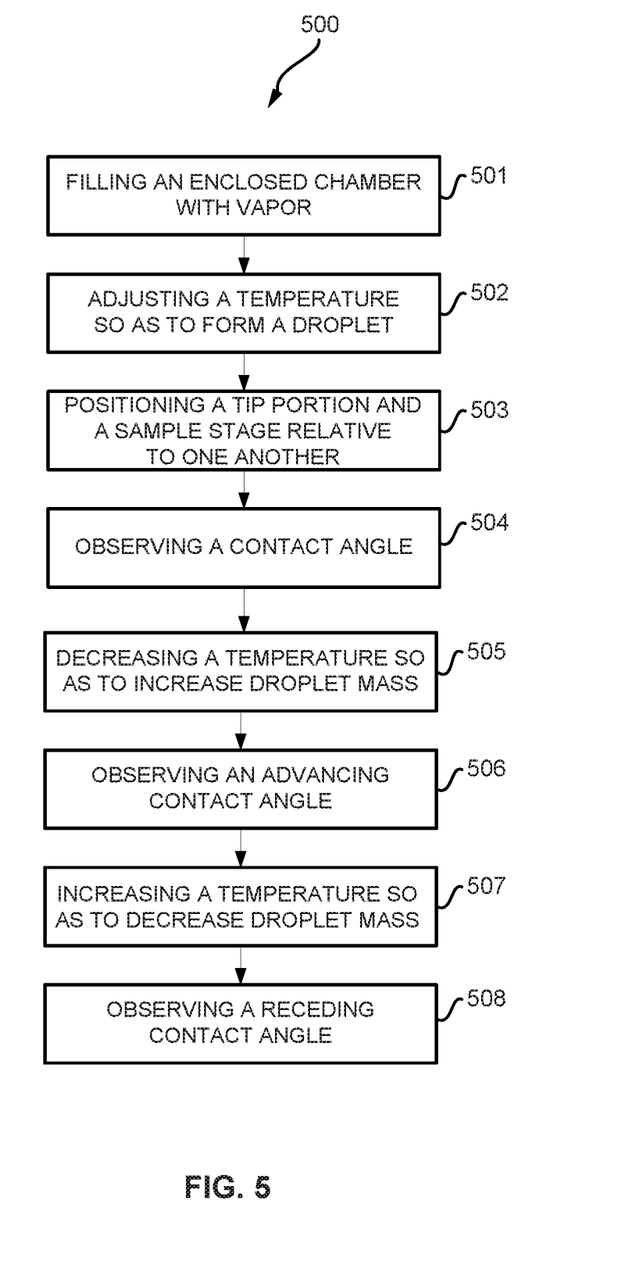
FIG. 5 illustrates a method of using a contact angle goniometer system in accordance with various embodiments.

In various exemplary embodiments and with reference now to FIGS. 4 and 5, a method 500 for using a contact angle goniometer system 400 comprises filling an enclosed chamber 406 with vapor 212 (step 501). The vapor 212 and/or enclosed chamber 406 may be subject to pressures and temperatures departing significantly from ambient. The temperature of a thermal conductor 206 is adjusted so as to form a droplet 208 of condensate on a tip portion 214 of the thermal conductor (step 502). The tip portion 214 and a sample stage 402 may be positioned relative to one another such that droplet 208 simultaneously contacts the thermal conductor 206 and a sample material 404 (step 503). A contact angle between droplet 208 and sample material 404 is observed (step 504).

In certain exemplary embodiments, method 500 may further comprise decreasing the temperature of the thermal conductor 206 so as to cause an increase in the volume and/or mass of droplet 208 (step 505), and observing an advancing contact angle between droplet 208 and sample material 404 (step 506). In certain exemplary embodiments, method 500 may further comprise increasing the temperature of the thermal conductor 206 so as to cause partial evaporation of droplet 208 (step 507). Partial evaporation of droplet 208 may correspond to a decrease in volume and/or mass of droplet 208. In certain exemplary embodiments, method 500 may further comprise observing a receding contact angle between droplet 208 and sample material 404 (step 508).

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

When a phrase similar to "at least one of A, B, or C" or "at least one of A, B, and C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

What is claimed is:

1. A method of using a contact angle goniometer system, the method comprising:
    filling an enclosed chamber of the contact angle goniometer system with vapor;
    adjusting a temperature of a thermal conductor so as to form a droplet of condensate on a tip portion of the thermal conductor;
    positioning the tip portion and a sample stage relative to one another such that the droplet simultaneously contacts the tip portion and a sample material; and
    observing a contact angle between the droplet and the sample material.

2. The method of claim 1, further comprising:
    decreasing the temperature of the thermal conductor so as to cause an increase in the mass of the droplet; and observing an advancing contact angle between the droplet and the sample material.

3. The method of claim 1, further comprising:
increasing the temperature of the thermal conductor so as to cause a decrease in the mass of the droplet; and
observing a receding contact angle between the droplet and the sample material.

4. The method of claim 1, wherein the temperature of the thermal conductor is adjusted via a peltier heat pump.

5. The method of claim 1, wherein the temperature of the thermal conductor is adjusted via an indirect contact heat exchanger.

6. The method of claim 1, wherein the tip portion is generally square in shape.

7. The method of claim 1, wherein the tip portion is generally conical in shape.

8. The method of claim 1, wherein the contact angle goniometer system comprises:
a camera positioned so as to capture images of the droplet in contact with the sample material; and
a light-generating component positioned so as to illuminate the droplet in contact with the sample material.

9. The method of claim 1, further comprising varying a temperature of the sample stage.

10. The method of claim 9, wherein the temperature of the sample stage is varied by at least one of a thermoelectric element, a peltier heat pump, or a circulating thermal fluid.

11. The method of claim 1, wherein the vapor comprises at least one of: (i) methane at a temperature less than 162 Kelvin and a pressure greater than 101 kiloPascals (kPa); (ii) ethane at a temperature less than 300 Kelvin and a pressure greater than 1 megaPascal (MPa); (iii) butane at a temperature less than 320 Kelvin and a pressure greater than 0.5 MPa; (iv) propane at a temperature less than 300 Kelvin and a pressure greater than 1 MPa; or (v) carbon dioxide at a temperature less than 250 Kelvin and a pressure greater than 2.5 MPa.

12. The method of claim 1, wherein the enclosed chamber is configured to withstand an internal pressure of up to 30 atmospheres (3.04 megaPascal).

* * * * *